United States Patent
Stess et al.

(10) Patent No.: US 6,808,501 B2
(45) Date of Patent: Oct. 26, 2004

(54) CUSTOM MOLDED WRIST AREA IMPRESSION KIT AND METHOD

(76) Inventors: Richard M. Stess, 36 Dutch Valley La., San Anselmo, CA (US) 94960; Peter M. Graf, 566 11$^{th}$ Ave., San Francisco, CA (US) 94118

( * ) Notice: Subject to any disclaimer, the term of this patent is extended or adjusted under 35 U.S.C. 154(b) by 0 days.

(21) Appl. No.: 10/277,274

(22) Filed: Oct. 22, 2002

(65) Prior Publication Data

US 2004/0077980 A1 Apr. 22, 2004

(51) Int. Cl.$^7$ .................................................. A61F 5/00
(52) U.S. Cl. .................................. 602/6; 602/5; 128/90
(58) Field of Search ...................... 602/5, 8, 6; 128/90; 428/230, 251

(56) References Cited

U.S. PATENT DOCUMENTS

| | | |
|---|---|---|
| 3,656,475 A | 4/1972 | Hanrahan, Jr. |
| 4,019,506 A | 4/1977 | Eschmann |
| 4,129,127 A | 12/1978 | Ellison |
| 4,683,877 A * | 8/1987 | Ersfeld et al. ................. 128/90 |
| 4,793,330 A * | 12/1988 | Honeycutt et al. ............. 602/8 |
| 5,228,164 A | 7/1993 | Graf et al. |
| 5,409,448 A * | 4/1995 | Kelley ........................... 602/5 |
| 5,514,080 A | 5/1996 | Blott et al. |

* cited by examiner

*Primary Examiner*—Henry Bennett
(74) *Attorney, Agent, or Firm*—Robert B. Chickering; Dorsey & Whitney LLP

(57) ABSTRACT

Custom molded wrist area impression sleeve (21) having a configuration substantially covering the wrist area (WA) of a patient. The impression sleeve (21) is formed from a thin, resin-impregnated, resilient fabric sleeve (21) mounted over a thin, flexible, resin-impervious release layer (23), and preferably over a cushioning and thermally insulating foam sleeve (25). The hardenable sleeve (21) can include one, and preferably two, longitudinally extending weakened strips (30, 40) which facilitate severing and act as a hinge (40) for the resulting hardened wrist brace. In the present method, the wrist area impression sleeve (21) is hardened on the patient's wrist, cut off and then used as a removable brace or to form a custom orthosis in a fabrication laboratory.

4 Claims, 2 Drawing Sheets

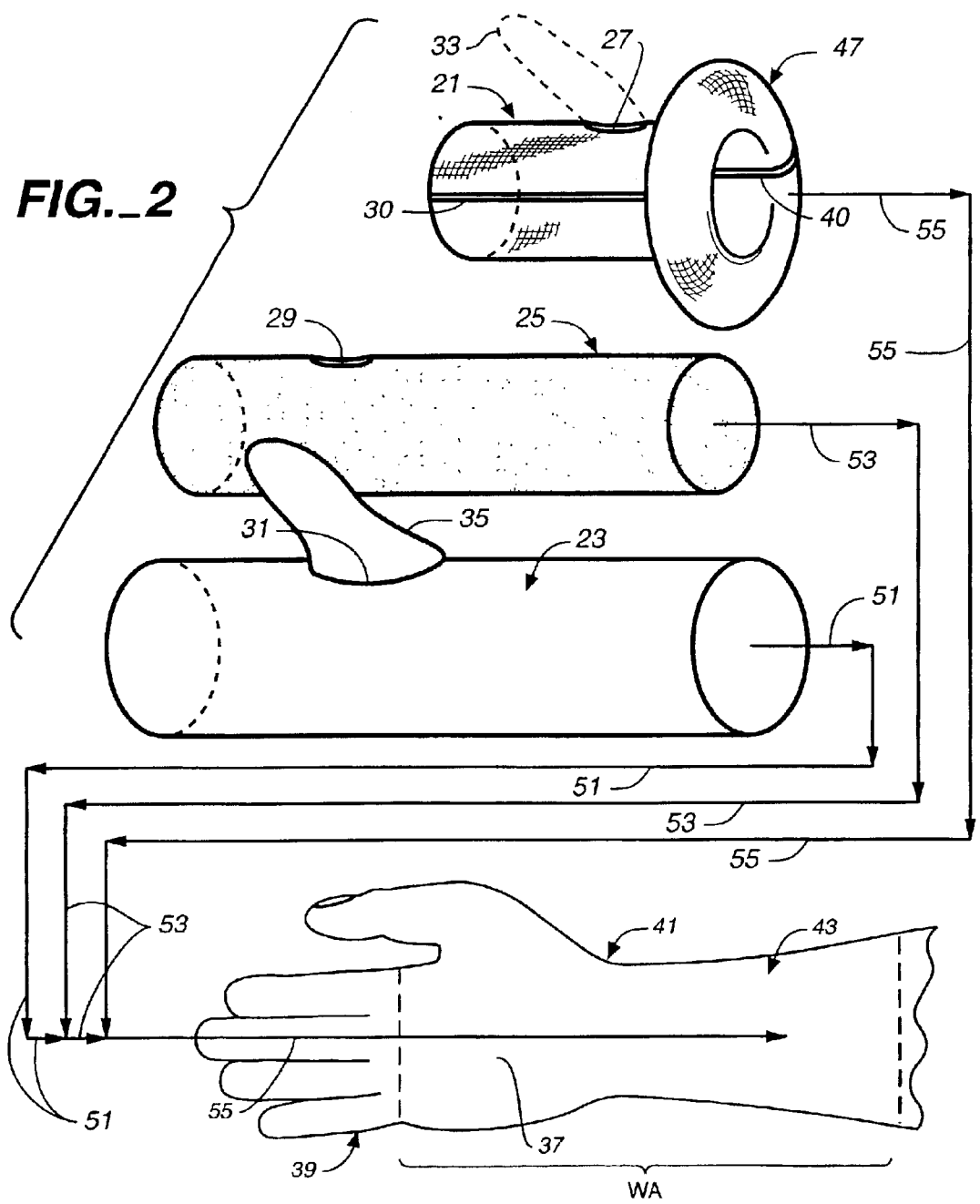

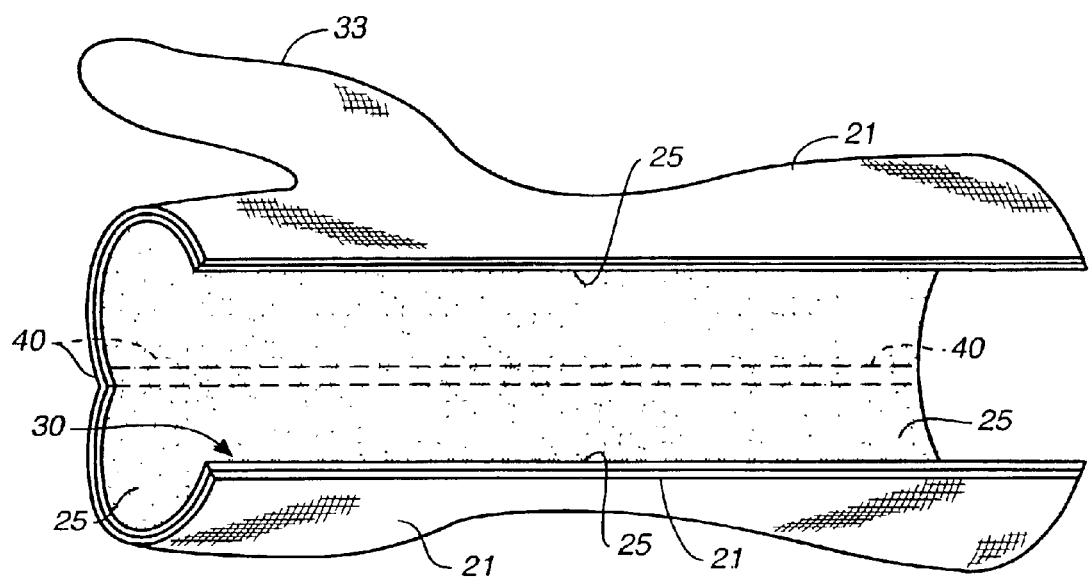
FIG._3

CUSTOM MOLDED WRIST AREA IMPRESSION KIT AND METHOD

TECHNICAL FIELD

This invention relates, in general to custom molded orthopedic braces, and more particularly, relates to methods and apparatus for the formation of a custom molded impression of a patient's wrist area which can be used to form an immobilization cast or wrist brace.

BACKGROUND ART

Custom casting of a patient's wrist area can be employed to effect relatively complete immobilization of the wrist, for example, to heal a broken bone, or merely to limit wrist motion, for example, to treat carpal tunnel syndrome or to prevent over-extension of the wrist while performing various tasks. Motocross motorcycle riders, for example, are at risk for painful wrist injuries as a result of dynamic shock loads which can over-extend the wrist, pulling or tearing ligaments and tendons. A removable custom molded wrist brace which permits limited motion and yet will resist extreme wrist articulation under dynamic loading would be highly desirable for such activities.

As used herein, the expression "wrist area" shall be understood to include the area extending from a patient's forearm across the wrist to a position over the patient's hand.

Considerable effort has been directed toward the formation of orthopedic immobilizing casts or braces for various portions of patients' anatomies, most usually limbs. To the extent that immobilizing casts or braces are formed for limbs, the cast and/or brace must be sufficiently rigid to support and/or immobilize the portion of the patient to which the cast is applied. This, in turn, usually requires that casts or braces be formed of a multiplicity of layers of material to provide the necessary strength and rigidity for immobilization.

Typical of the prior art multi-layered immobilization casting systems are the orthopedic casts shown in U.S. Pat. Nos. 5,514,080; 4,683,877; 4,129,127; 4,019,506; and 3,656,475. Since these systems employ multiple layers and various combinations of hardening materials, they are tedious and difficult to form on the patient in order to achieve the highly desirable custom fit. Such custom casting, it will be understood, is often undertaken when the patient is in pain or experiencing considerable discomfort, making the construction of a cast in situ a disagreeable experience.

Moreover, part of a casting process often requires that at least a portion of the patient be held or maintained in a desired position during casting so that the eventual cast will support the patient as needed. As the casting time becomes longer due to the complexity of forming a cast with sufficient rigidity to support the patient, it is more difficult to maintain the desired patient orientation or positioning. Since in situ casting is often accomplished using resins which produce considerable heat during rigidification, another problem is providing sufficient thermal insulation between the patient and the various casting layers, which can contain a substantial volume of resin. Many casting resins experience exothermic curing. The thermal insulation required to withstand exothermic resin curing again makes the process of in situ casting more complex and tedious, as well as interposing layers between the patient and the eventual rigid cast which can affect cast fit.

Less has been done in the area of custom molded braces which permit some motion but provide the user with support which will avoid further injury (carpal tunnel syndrome) or which prevent injury to the wrist from over-extension. Such braces are desirably light in weight and removable for ease of use.

One wrist area custom molded cast system in which the cast can be selectively mounted to the patient's wrist and removed is being commercially exploited by Distrac Ortho-Medical Supplies of Hoegaarden, Belgium, under the trademark ZIP-Y-CAST. The ZIP-Y-CAST system is mounted from the side of the arm to the patient's wrist area and which includes a resin molded cast which incorporates a zipper or VELCRO hook and loop fastener structure to close the longitudinally extending, open side of the cast. The molding system, however, is messy in its use, requiring the pouring of the hardening resin between two fabric sleeves and thereafter dispersing of the resin evenly throughout the casting fabrics before hardening using a roller.

Accordingly, it is an object of the present invention to provide a custom molded wrist impression kit and method that can be used to mold an impression of a patient's wrist area which can be used as a custom, rigid, immobilizing brace as a removable, motion-limiting, support brace.

A further object of the present invention is to provide a method of forming a custom molded wrist area impression kit which is suitable for home use as well as use by medical technicians.

A further object of the present invention is to provide a kit for and a method of forming, a custom molded wrist area impression cast that can be easily removed and remounted to the patient's wrist area and has sufficient flexure for limited hand motion and sufficient rigidity to resist wrist over-extension.

Still a further object of the present invention is to provide a custom molded wrist area impression cast and method which are suitable for scanning to enable the subsequent formation of an immobilizing wrist cast.

Still a further object of the present invention is to provide a custom molded wrist are impression cast and method for formation of the same, which is easily removed after casting, can include a cushioning layer, and can be selectively cast to be relatively rigid or relatively flexible, depending upon its use.

The custom molded wrist are impression kit and method of the present invention have other objects and features of advantage which will become apparent from, or are set forth in more detail in, the accompanying drawing and the following description of the Best Mode of Carrying out the Invention.

DISCLOSURE OF INVENTION

The custom molded wrist area impression kit of the present invention comprises, briefly, an elongated tubular fabric impression sleeve having a configuration substantially covering the wrist area of a patient and a thumb-receiving opening therein. The sleeve has sufficient elasticity to enable mounting over the patient's hand onto the wrist area and thereafter to conform to the patient's wrist area. The kit also includes a quantity of curable resin, preferably impregnated in the impression sleeve, sufficient to rigidify the impression sleeve. Most preferably the impression sleeve includes a weakened strip extending longitudinally from one end to the other to facilitate severing of the hardened sleeve and its removal after casting. A second weakened strip on an opposite side of the cast can provide a line hinge for articulation of the hardened sleeve to permit its removal and remounting.

The method of forming a custom molded wrist area impression brace of the present invention comprises, briefly, the step of mounting a tubular, elastic, hardenable, impervious sleeve over a patient's hand to a position across the wrist area, manipulating the wrist area to a desired orientation, and hardening a resin in the impression sleeve while the patient's wrist area is in the desired orientation.

The present method further preferably includes the step of removing the hardened impression sleeve by cutting the hardened impression sleeve along a weakened strip in a side of the impression sleeve and resiliently outwardly displacing the cut hardened impression sleeve, preferably about a second weakened strip on an opposite side of the impression sleeve.

BRIEF DESCRIPTION OF THE DRAWINGS

FIG. 1 is a side elevation schematic view of an impression sleeve constructed in accordance with the present invention and shown in a rolled out condition prior to molding.

FIG. 2 is a schematic, side elevation, pictorial view of the custom molding steps and apparatus of the wrist area impression method and kit of the present invention.

FIG. 3 is a side elevation pictorial representation of a hardened custom molded wrist area impression cast opened up for mounting on or removal from the patient's wrist area.

BEST MODE OF CARRYING OUT THE INVENTION

The wrist area impression sleeve, kit and method of the present invention are particularly well suited for formation of a hardened, removable wrist brace that can be custom molded at home by the patient or brace user. The same kit, however, also can be used to make an immobilizing orthopedic cast by medical personnel, either directly on the patient or in the laboratory after removal of the hardened casting sleeve.

Referring now to the drawing, the present wrist area impression kit for custom molding of a wrist brace is based upon the use of a relient, elongated, tubular, hardenable impression sleeve 21. As will be seen in FIG. 2 and as is set forth hereinafter below, sleeve 21 may be used with various other components such as release member or tube 23, and/or cushioning sleeve 25.

Impression sleeve 21 of the present invention can advantageously be formed of synthetic fabric material, such as lofted glass yarn or polyester yarn, and it is preferably knit with elastomeric yarn that provides transverse resiliency for the sleeve. It is preferable that the sleeve fabric exhibit extensibility of about 100% in a direction transverse to a longitudinal axis of the sleeve. This will allow the sleeve to be mounted over the user's or patient's hand and yet conform to the wrist area of the patient.

Most preferably the present impression sleeve is used with a quantity of water-curable resin sufficient to harden the entire sleeve. This enables the user or technician to remove a resin soaked impression sleeve 21 from its storage container, dip it in a bucket or container of water and apply it to the patient's wrist area. Alternatively, the sleeve can be positioned on the patient's wrist area and the resin activated or hardened by spraying the sleeve with water while on the wrist area. Dipping the sleeve in water prior to application to the wrist is preferred. A further alterative is to apply the sleeve in a dry condition and then paint or spray the resin on the sleeve, followed by spraying or dipping in water.

Sleeve materials and resins which are suitable for use in practicing the present invention are set forth in our U.S. Pat. No. 5,228,164, which disclosure is incorporated herein by reference in its entirety. The shell-forming fabric and water curable resin of our U.S. Pat. No. 5,228,164 were originally created for the formation of lasts for custom footwear, but they also are suitable for use in the wrist area brace impression kit of the present invention.

Since the kit of the present invention is designed to enable fabrication of custom molded wrist braces or casts, impression sleeve 21, and sleeves or tubes 23 and 25, are each preferably formed with a thumb-receiving opening 27, 29 and 31 therein proximate one end of the sleeves. Optionally a thumb-receiving pocket 33 (shown in broken lines) of resiliently elastic material can be provided on fabric sleeve 21. Cushioning sleeve 25 can have a similar pocket (not shown), as can release sleeve 23 which has a pocket 35 shown in solid lines.

The resilient hardened wrist brace need not include thumb pocket 33, but it is advantageous for release sleeve 23 always to include pocket 35 simply to keep resin from contacting the patient's skin. This would be true of sleeve 25 if it is used instead of sleeve 23 as the resin impervious layer, as will be described below.

Impression sleeve 21 should have a length sufficient to extend from a position covering a portion, usually palm 37 of the user's hand 39, across wrist 41 to a position over at least a portion of the patient's forearm 43. Sleeve 21 can optionally extend to the user's elbow, but such an extended length is normally not necessary or desirable to limit motion of, or to immobilize, the wrist.

In one embodiment of the present invention, sleeve 21 is formed of lightweight or low denier knit yarn so that the hardened cast will be somewhat flexible so as to permit limited hand and wrist motion. Thus, when a removable wrist brace is to be fabricated, the yarn denier can be below about 150 so that when the resin is hardened, the brace still will flex. This type of wrist brace can be used, for example, to limit hand motion which will exacerbate carpal tunnel syndrome and yet will permit tasks such as typing. Similarly, in motocross applications, over-extension of the wrist area in a rearward direction can be prevented or at least resisted by the present brace, while limited hand motion necessary to drive the motorcycle is permitted.

A knit sleeve suitable for use in the present invention would be a base yarn of 100 denier polyester wrapped around a 40 denier Spandex core. This base yarn can be knit with 150 denier polyester yarn in a terry knit.

In another aspect of the present invention, a wrist immobilization cast results which can limit motion in the wrist area sufficiently to allow broken bones to heal. This type of cast can be made using either of two types of sleeves 21. First, a low denier yarn sleeve can be employed and the resulting hardened, custom molded shell removed from the patient and taken to a laboratory for scanning and formation of a strong immobilization cast.

Alternatively, a sleeve 21 formed from relatively high denier yarn can be employed, and the hardened cast used directly as the immobilizing wrist area brace. Even when the hardened impression sleeve is used directly as a immobilization brace, it is often desirable to remove the cast for reinforcing to enable substantially complete immobilization of the wrist area.

Thus, removal of impression sleeve 21 from the patient's wrist area and remounting to the wrist area are frequently desirable or absolutely necessary, depending on the application. Accordingly, it is a feature of the impression sleeve 21 of the present invention that it be provided with one, and preferably two, longitudinally extending weakened strips 30 and 40 that extend along opposite sides of sleeve 21, preferable over the full length of sleeve 21.

Weakened strips 30, 40 can be provided by omitting or spacing one or more warp yarns on the sleeve during knitting so that there will be less fabric along strips 30, 40 to which resin can bond and harden. The result will be that pairs of adjacent longitudinally extending warps will be spaced apart, particularly when transversely stretched over the wrist area, so that the hardened shell or impression sleeve 21 will have longitudinally extending weakened strips on opposite sides of the cast.

One of strips 30, 40 can be used for severing of the hardened shell or sleeve, while the other strip can be used as a hinge about which the hardened shell can be articulated, as best seen in FIG. 3.

Referring now to FIG. 2, additional components of the wrist area impression kit of the present invention can be described, as well as the method of the present invention.

In the preferred form the impression kit includes a resin barrier which prevents contact of the resin in sleeve 21 with the patient's arm. Such a barrier preferably can be provided by either or both of sleeves 23 and 25. In the broadest aspect such a barrier also could be a material sprayed or painted on the patient's wrist area.

Sleeve or member 23 can be a thin, flexible release sleeve with a thumb pocket 35 and optionally finger pockets, not shown. Thus, member 23 can be provided by a polyethylene sleeve, bag or glove having a thickness of 0.005 inches or less which is sized and shaped to substantially conform to the user's hand and wrist area. If a tube or bag 23 is used, as shown in FIG. 2, there will be some wrinkles under impression sleeve 21, which will not be significant in light of the thin nature of the tube. Tube 23 preferably is longer than sleeve 21 so as to provide resin protection at both ends of sleeve 21. Release layer 23 also could be provided as a wrap rather than a tube or sleeve. Since polyethylene does not have great elasticity, tube 23 also generally will have a larger diameter than impression sleeve 21.

In FIG. 2 an optional element of the impression kit also is shown, namely, a cushioning thermal insulating and resin barrier tubular member 25. Sleeve 25 also can advantageously be provided as a tube of resiliently elastic foamed material. Tube 25 may be placed over release tube 23 and under hardenable impression sleeve 21. Moreover, tube 25 also could be provided as a strip of material that is wrapped around wrist area WA, but such an approach is less desirable in light of the overlapping edges which increase cast bulk and decrease smoothness, as well as being more tedious in nature to apply.

It also is possible to eliminate release layer 23 and merely provide the foam tube as a closed cell foam which will act as a barrier to resin migration into contact with the patient's skin.

Foam sleeve 25 can be an open or closed cell polyurethane foam which will have a diameter less than the diameter of the patient's wrist area and is transversely resiliently extensible for mounting on the wrist area over the patient's/user's hand 39. Sleeve 25 will then closely resiliently conform to the wrist area. Tube 25 also can be longer than sleeve 21 to afford resin protection at the ends of sleeve 21. Sleeve 25 can provide three functions, namely, cushioning, thermal insulation and a resin barrier. Since curing of most casting resins will be based upon an exothermic reaction, foam layer 25 prevents uncomfortable heat transfer to the patient as the resin hardens sleeve 21.

As schematically shown in FIG. 2, therefore, release tube or glove 23 can optionally be mounted over hand 37 and on to wrist area (WA), as indicated by arrow 51. The thumb of the user will be positioned in pocket 35.

Next, either foam sleeve 25, or fabric impression sleeve 21, will be mounted over member 23. If cushioning is desired in the resulting brace, foam sleeve 25 is mounted over hand 39, as indicated by arrow 53 and the user's thumb inserted through thumb-receiving opening 29 (and into a foam pocket if one is provided).

Sleeve 21 is shown in FIG. 1 in an unrolled condition, but in the most preferred form, the fabric impression sleeve initially is saturated/impregnated with a water curable resin and rolled up from the forearm end 45 to a position proximate or even beyond thumb-receiving opening 27, as shown in FIG. 2. If sleeve 21 has a thumb pocket 33, the pocket also can be rolled onto the roll 47 shown in FIG. 2. The curable resin can be carried by the rolled up fabric impression sleeve and the sleeve stored in a rolled up condition in an airtight foil envelope or other container. The transverse elasticity of knit sleeve 21 allows the same to be placed over the patient's hand 39, as indicated by arrow 55. Once the thumb is positioned through opening 27 and in pocket 33, if there is a pocket, impression sleeve 21 is unrolled over sleeves 23 and 25 to the positions shown in broken lines in FIG. 2. The user or casting technician can then smooth and conform the elastic impression sleeve to the patient's wrist area while the resin is in an uncured condition. The elasticity of the sleeve fabric combines with manual smoothing by the user or technician to allow sleeve 21 to conform closely to the patient's wrist area.

Once the impression sleeve has been smoothed down over the patient's wrist area, water can be applied to the sleeve, using a spray bottle or other water applicator, so as to cause the resin to begin curing. Before starting the curing process, or soon after it has been started, the user or technician will manipulate or position the patient's wrist area in a desired orientation for formation of the impression cast. If there is an orientation in which the eventual brace is to support or immobilize the patient, that orientation of the wrist area need only be maintained during the resin curing stage, not the complete build-up of an immobilization case. Resin curing can be relatively short because the quantity of resin on the impression sleeve can be relatively small. Thus, in as little as 4–6 minutes, the impression sleeve will be sufficiently hard so as to be self supporting. This means that the patient need no longer be tediously held or positioned in the desired orientation, and the impression sleeve will start to provide some support for the patient in the desired position as it cures.

Since in many applications it is desirable to make the resultant wrist brace removable and cushioned one of the advantages of the kit of the present invention is that the cushioning and thermal insulating sleeve 25 will bond to impression sleeve 21 during curing. Such bonding will cause cushioning layer 25 to remain with the hardened sleeve when the cast is opened up, as shown in FIG. 3.

The next step in the method of the present invention is to remove hardened impression sleeve 21 from the patient's wrist area. This can be accomplished by cutting the hardened impression sleeve 21 and underlying foam sleeve 25 and release glove 23 along a side of the molded or hardened sleeve. Cutting can be accomplished by scissors, a knife or a cast saw, if a protector is positioned between the sleeve and wrist area.

Sleeve removal optionally can be facilitated by weakened strips 30 and 40, and severing is most preferably accomplished along weakened strip 30 on the inside of the cast, as can be seen from FIG. 3. Once cut along weakened strip 30, the hardened cast can be resiliently outwardly displaced about the other weakened strip 40, which acts as a hinge, and the wrist cast assembly can be removed from the patient.

If the hardened impression sleeve assembly is to be used as part of a process for making an immobilizing cast, the hardened thin shell which is produced is of uniform thickness, and now can be used to form an orthosis (orthopedic wrist brace or orthopedic cast) in the laboratory. The hardened impression sleeve or shell can be used in a number of different ways to form the orthosis. One approach is to scan impression sleeve 21 using a digital scanner. A digital scanner can be used to scan the outside of the impression sleeve, or to scan the inside of the sleeve, particularly if no cushioning layer has been used. Since the impression sleeve does not employ wraps, as is the case for casting tape, it is thin and of uniform in thickness. Scanning the outside of the hardened impression sleeve, and digital removal of the known thickness of the shell, can be used to obtain digital data as to the inside surface, as it was custom molded to the patient's wrist area. Cut line 30 can be secured back together by fasteners, such as tape or adhesives. Impression scanning equipment are well known in the orthopedic industry for capturing sufficient digital data to enable creation of an orthosis from hardened impression sleeve 21. The scanned data also can be digitally adjusted to accommodate an orthosis liner or padding on the inside of the orthosis.

Another approach to forming a wrist orthosis from hardened impression sleeve 21 would be to fill the inside of sleeve 21 with a supporting foam or plaster of Paris and then form the orthosis over a part or all of the supported sleeve 21. The thin nature of sleeve 21 allows the orthosis formed over it to be only slightly padded, which is desirable in any event, in order to produce a close custom fit.

An additional approach to making an orthosis using a hardened impression sleeve 21 is to essentially build the orthosis over impression sleeve 21. Thus, reinforcing layers can be placed over impression sleeve 21. The outer layers can have substantial strength and include, for example, substantial quantities of resin, heavy fabrics and even reinforcing plates or the like. Since this work is done in a laboratory, there is no problem with exothermic reactions being uncomfortable for the patient or in connection with positioning of reinforcing layers and materials in the cast, which would be tedious if the patient had to maintain a desired wrist area orientation.

Finally, hardened sleeve 21 also can be used to make a positive mold inside the shell, particularly when no cushioning is used, for example, by using plaster of Paris. The shell can be reinforced exteriorly while the positive is made so as to maintain the molded dimensions, and then shell or sleeve 21 is removed from the cast positive. An orthosis is then formed over the positive mold in the laboratory.

Thus, the present invention allows a hardened wrist area impression sleeve to be used as a shell for the formation of a custom molded orthosis in the laboratory.

An important additional use of hardened impression sleeve 21 of FIG. 3 is simply to use the FIG. 3 assembly is as a removable brace. Foam layer 25 will enable some movement inside the brace and shell or sleeve 21 will be thin enough to flex to enable additional limited wrist area motion.

The brace assembly of FIG. 3 can be simply closed around the user's wrist area and held in a closed position by an elastic bandage or by an openably fastener arrangement such as arm encircling strays (not shown) with Velcro or other fasteners.

For motocross use the wrist area would be cast, usually without thumb pocket 33, in an orientation allowing the rider to accelerate and steer the motorcycle, while for carpal tunnel syndrome the wrist area would be cast in nerves in the wrist.

What is claimed is:

1. A wrist area impression kit for custom molding of a wrist brace comprising:

(a) an elongated tubular impression sleeve formed of a resilient terry knit fabric material having sufficient length to extend from a position over a portion of the patient's hand across the patient's wrist to a position over a portion of the patient's forearm, the sleeve having a thumb-receiving opening therein proximate one end, the terry knit fabric material having sufficient radial resiliency to be mounted over the patient's hand onto the patient's wrist to thereafter conform to the patent's hand, wrist and forearm over the length of the sleeve, and the terry knit fabric having a weakened strip provided by a pair of adjacent fabric warps laterally spaced apart by a distance more than an average lateral warp spacing for other warps in the sleeve extending longitudinally from one end of the sleeve to an opposite end of the sleeve to facilitate severing of the sleeve after casting; and (b) a quantity of curable resin sufficient to rigidify the sleeve into a hardened impression cast provided in one of a container separate from the sleeve and directly on the sleeve.

2. A wrist area impression kit for custom molding of a wrist brace comprising:

(a) an elongated tubular impression sleeve formed of a resilient fabric material having sufficient length to extend from a position over a portion of the patient's hand across the patient's wrist to a position over a portion of the patient's forearm, the sleeve having a thumb-receiving opening therein proximate one end, the fabric material having sufficient radial resiliency to be mounted over the patient's hand onto the patient's wrist to thereafter conform to the patent's hand, wrist and forearm over the length of the sleeve, and the sleeve is formed with two longitudinally extending weakened strips over the length of the sleeve with one weakened strip being suitable for severing after casting and the other weakened strip being suitable to act as a longitudinally extending hinge after casting; and (b) a quantity of curable resin sufficient to rigidify the sleeve into a hardened impression cast provided in one of a container separate from the sleeve and directly on the sleeve.

3. A wrist area impression kit for custom molding of a wrist brace comprising:

(a) an elongated tubular impression sleeve formed of a resilient fabric material having sufficient length to extend from a position over a portion of the patient's hand across the patient's wrist to a position over a portion of the patient's forearm, the sleeve having a thumb-receiving opening therein proximate one end, the fabric material having sufficient radial resiliency to be mounted over the patient's hand onto the patient's wrist to thereafter conform to the patent's hand, wrist and forearm over the length of the sleeve, and a fabric pocket is attached to the sleeve at the thumb-receiving opening; and (b) a quantity of curable resin sufficient to rigidify the sleeve into a hardened impression cast provided in one of a container separate from the sleeve and directly on the sleeve.

4. The impression kit as defined in claim 3 wherein, the fabric pocket is a radially elastic pocket formed to conform to the thumb of the patient.

* * * * *

UNITED STATES PATENT AND TRADEMARK OFFICE
CERTIFICATE OF CORRECTION

PATENT NO. : 6,808,501 B2
DATED : October 26, 2004
INVENTOR(S) : Richard M. Stess et al.

It is certified that error appears in the above-identified patent and that said Letters Patent is hereby corrected as shown below:

Column 7,
Line 63, after "would be cast in", insert -- a typing orientation that would not allow pinching of --.

Signed and Sealed this

Twenty-third Day of August, 2005

JON W. DUDAS
*Director of the United States Patent and Trademark Office*